United States Patent
Uretsky et al.

(10) Patent No.: US 10,073,104 B2
(45) Date of Patent: Sep. 11, 2018

(54) CONTROL OF PH IN AQUEOUS UREA-CONTAINING SOLUTIONS UTILIZING AMINO ACID-CONTAINING COMPOSITIONS

(71) Applicant: Siemens Healthcare Diagnostics Inc., Tarrytown, NY (US)

(72) Inventors: Laura Uretsky, Milford, MA (US); Kevin Horan, Raynham, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 161 days.

(21) Appl. No.: 14/775,325

(22) PCT Filed: Mar. 13, 2014

(86) PCT No.: PCT/US2014/025231
§ 371 (c)(1),
(2) Date: Sep. 11, 2015

(87) PCT Pub. No.: WO2014/159816
PCT Pub. Date: Oct. 2, 2014

(65) Prior Publication Data
US 2016/0025754 A1 Jan. 28, 2016

Related U.S. Application Data

(60) Provisional application No. 61/782,851, filed on Mar. 14, 2013.

(51) Int. Cl.
*G01N 33/96* (2006.01)
*C12Q 1/58* (2006.01)
*G01N 33/84* (2006.01)
*A61K 38/00* (2006.01)

(52) U.S. Cl.
CPC ............ *G01N 33/96* (2013.01); *A61K 38/00* (2013.01); *C12Q 1/58* (2013.01); *G01N 33/84* (2013.01); *C12Q 2527/119* (2013.01); *G01N 2496/00* (2013.01)

(58) Field of Classification Search
CPC . C07K 1/006; C07K 1/00; C12N 9/96; C12N 9/00; G01N 33/96; G01N 33/50; G01N 33/48; G01N 21/278; G01N 21/274; G01N 21/27; G01N 27/16
USPC .................... 436/8; 435/68.1; 530/332, 409
See application file for complete search history.

(56) References Cited

U.S. PATENT DOCUMENTS

| | | | |
|---|---|---|---|
| 4,273,786 A | 6/1981 | Kraskin | |
| 4,605,513 A | 8/1986 | DiMarchi | |
| 6,136,607 A | 10/2000 | Conlon et al. | |
| 6,303,656 B1 | 10/2001 | Burnier | |
| 6,355,259 B1 | 3/2002 | Hiraki et al. | |
| 6,632,675 B1 | 10/2003 | Conlon et al. | |
| 7,459,425 B2 | 12/2008 | Wan et al. | |
| 7,705,765 B1 | 4/2010 | Yang | |
| 2004/0137633 A1 | 7/2004 | Shin et al. | |
| 2005/0032153 A1 | 2/2005 | Ropp et al. | |
| 2012/0007022 A1 | 1/2012 | Ropp et al. | |

FOREIGN PATENT DOCUMENTS

| | | | |
|---|---|---|---|
| JP | 55122753 | 9/1980 | |
| JP | 58026809 | 2/1983 | |
| JP | 58194805 | 11/1983 | |
| JP | 59134707 | 8/1984 | |
| JP | 59134772 | 8/1984 | |
| JP | 60185757 | 9/1984 | |
| JP | 61030567 | 2/1986 | |
| JP | 61033161 | 2/1986 | |
| JP | 61204159 | 9/1986 | |
| JP | 61207306 | 9/1986 | |
| JP | 62048613 | 3/1987 | |
| JP | 5163129 | 6/1993 | |
| JP | 9124434 | 5/1997 | |
| JP | 10139619 | 5/1998 | |
| JP | 2002363023 | 12/2002 | |
| JP | 2003119105 | 4/2003 | |
| WO | WO 2012/028315 A1 * | 3/2012 | ............... A61K 9/19 |

OTHER PUBLICATIONS

McMenamy, et al., "Unbound Amino Acid Concentrations in Human Blood Plasmas", Dec. 1957; J Clin Invest., vol. 36(12), pp. 1672-1679.
Smyth, Derek G., "Carbamylation of Amino and Tyrosine Hydroxyl Groups", 1967, Issue of Apr. 10, The Journal of Biological Chemistry, vol. 242, No. 7, pp. 1579-1591.
Kraus, et al., "Carbamoylation of Amino Acids and Proteins in Uremia", 2001, Kidney International, vol. 59, Suppl. 78, pp. S-102-S107.
Esadze, et al., "Dynamics of Lysine Side-Chain Amino Groups in a Protein Studied by Heteronuclear H-1-N-15 NMR Spectroscopy", 2011, Journal of The American Chemistry Society, vol. 133, pp. 909-919.
Jaisson, et al., "Carbamylation-Derived Products: Bioactive Compounds and Potential Biomarkers in Chronic Renal Failure and Atherosclerosis", Nov. 2011, Clinical Chemistry, vol. 57(11), pp. 1499-1505.
International Search Report and Written Opinion of International Application No. PCT/US2014/025231 dated Aug. 15, 2014.
European Search Report and Written Opinion of European Application No. 14774121.9 dated Oct. 27, 2016.

\* cited by examiner

*Primary Examiner* — Christine T Mui
(74) *Attorney, Agent, or Firm* — Kyle D. Petaja

(57) ABSTRACT

Aqueous calibration or quality control reagents that include urea are disclosed; the reagents may further include at least one amino acid-containing composition to provide pH stability thereto. Methods of production and use thereof are also disclosed.

18 Claims, 14 Drawing Sheets

100 mg/dL BUN in Calibration Solutions, Ammonia Regulation by Amino Acids vs. No Amino Acid Control 100 mg/dL BUN in Calibration Solutions, Ammonia Regulation by Amino Acids vs. No Amino Acid Control

100 mg/dL BUN in Calibration Solutions, pH Stability Amino Acids vs. No Amino Acid Control

100 mg/dL BUN in Calibration Solutions, pH Stability Amino Acids vs. No Amino Acid Control

CONTROL OF PH IN AQUEOUS UREA-CONTAINING SOLUTIONS UTILIZING AMINO ACID-CONTAINING COMPOSITIONS

CROSS REFERENCE TO RELATED APPLICATIONS/INCORPORATION BY REFERENCE STATEMENT

This application is the US National Stage of International Application No. PCT/US2014/025231, filed Mar. 13, 2014 and claims the benefit thereof. The International Application claims the benefit of U.S. Provisional Application No. 61/782,851, filed Mar. 14, 2013. All of the applications are incorporated by reference herein in their entirety.

BACKGROUND

Liquid solutions are currently used in the calibration and quality control of sensors, and these reagents are typically stored in closed systems such as glass ampoules or laminate barrier pouches, where the barrier material serves to prevent interaction with the environment and thus maintain a predetermined amount of gas in the solution (see for example, U.S. Pat. No. 6,632,675, issued to Conlon et al. on Oct. 14, 2003; and U.S. Pat. No. 6,136,607, issued to Conlon et al. on Feb. 3, 1998; the entire contents of each of which are expressly incorporated herein by reference). However, the shelf life of these solutions may be limited as a result of degradation products, such as but not limited to, ammonia and carbon dioxide.

When urea is present in solution, it degrades into ammonia and carbon dioxide ($CO_2$), particularly upon storage for extended periods of time at non-refrigerated storage temperatures. Generation of ammonia within the solution significantly increases and destabilizes the pH of the solution, thus reducing the shelf life of the solution and limiting the temperature options available for storage of the solution.

Urea-containing solutions are also utilized for protein/peptide processing. Another urea degradation product, cyanate, can react with the proteins/peptides to be processed and thus interfere with the protein/peptide processing reaction. Carbamylation of a protein/peptide occurs when cyanate reacts with certain amino acid side chain functional groups, thus yielding a carbamylated protein/peptide derivative that may have different biological and/or antigenic properties when compared to the native protein/peptide. Methods of inhibiting protein carbamylation in urea-containing protein/peptide processing solutions have been disclosed (see, for example, U.S. Pat. No. 4,605,513, issued to DiMarchi on Aug. 12, 1986; U.S. Pat. No. 7,459,425, issued to Wan and Ropp on Dec. 2, 2008; and US Published Application Nos. 2005/0032153 and 2012/0007022, published to Ropp et al. on Feb. 10, 2005 and Jan. 12, 2012, respectively; the contents of each of which are incorporated herein by reference in their entirety). In these methods, a cyanate scavenger molecule is added to a 7-9 M urea protein/peptide processing solution (at a final concentration of 1 mM to 150 mM for the scavenger); examples of cyanate scavengers disclosed by these references include, but are not limited to, 1,2-ethylene diamine and 1,2-ethylene diamine-like materials; diethanolamine; amino acids and amino acid derivatives such as but not limited to, L-Arginine, L-Cysteine, L-Glycine, L-Histidine, L-Lysine, L-threonine, taurine, glycinamide, and 4-hydroxy-proline; the dipeptides glycylglycine (Gly-Gly), histidylglycine (His-Gly), and histidylglycine (His-Gly); and the tripeptide tri-glycine (Gly-Gly). However, the effect of a cyanate scavenger molecule on the pH of these high molarity urea solutions has not been determined.

Therefore, there is a need in the art for new and improved aqueous urea-containing reagent embodiments used in the calibration and quality control of sensors that provide pH control thereof and thereby exhibit extended shelf life and temperature storage options for the reagents.

DETAILED DESCRIPTION

Figure 1:
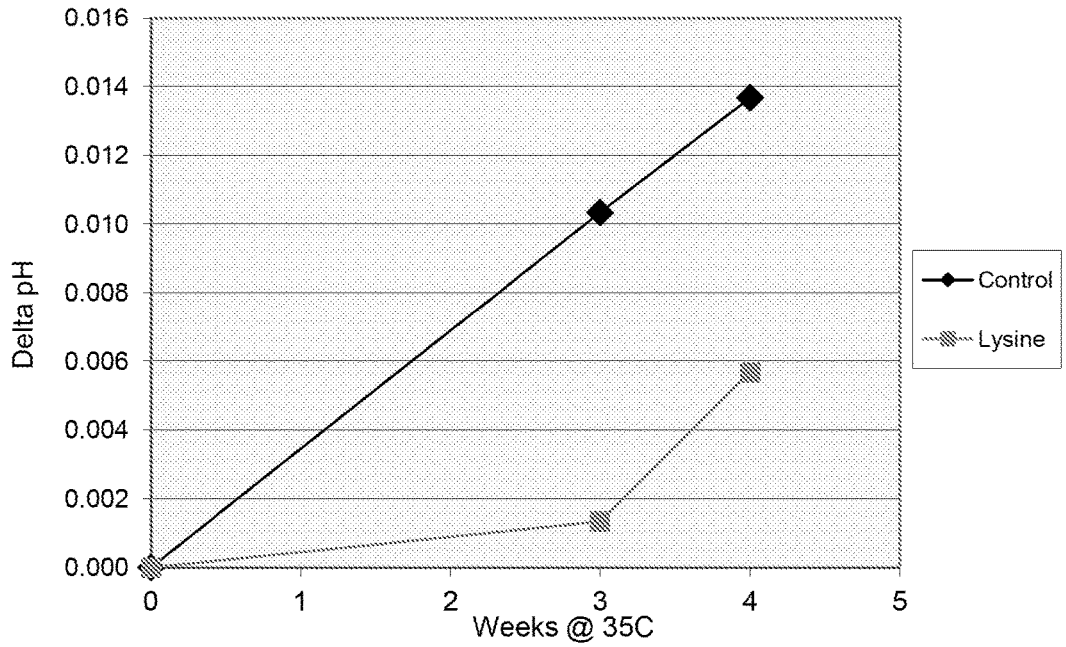
FIG. 1 graphically depicts the pH shifts observed in the urea-containing 200 Cal reagent in the presence or absence of lysine upon storage at 35° C. for various periods of time.

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses and chemical analyses.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions and/or methods disclosed and claimed herein can be made and executed without undue experimentation in light of the present disclosure. While the articles, compositions and methods of the inventive concept(s) have been described in terms of preferred embodiments, it will be apparent to those of skill in the art that variations may be applied to the articles, compositions and/or methods and in the steps or in the sequence of steps of the methods described herein without departing from the concept, spirit and scope of the inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

The term "about" is used to indicate that a value includes the inherent variation of error for the device, the method being employed to determine the value and/or the variation that exists among study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Turning now to the presently disclosed and claimed inventive concept(s), stabilization of pH in aqueous solutions containing urea is achieved by the addition of amino acid-containing compositions to the urea-containing solution. The addition of amino acid-containing compositions to the urea-containing solution provides a method to control pH and/or suppress ammonia formation in the solution from degradation of the urea present therein. In certain non-limiting embodiments, the urea-containing solutions are diagnostic calibration and/or quality control reagents. Reduction of urea by-products, such as ammonia and $CO_2$, provides multiple desired stabilization aspects to the solutions, including but not limited to, stabilization of reagent pH, urea, ammonia, $CO_2$, and bicarbonate concentrations, pH-dependent $Ca^{+2}$ and $Mg^{+2}$ chelation, and pH-dependent creatine:creatinine ratio. Better urea-containing reagent stability allows for higher urea targets and leads to more stable, accurate, and precise sensors, such as but not limited to, BUN sensors. As mentioned above, overall pH stability leads to stabilization of other pH dependent parameters within the formulation.

Amino acids are involved or related to those in the natural "Urea Cycle," which regulates ammonia concentrations in humans and other animals by forming urea. Amino acids may help stabilize urea in solution, thus slowing the formation of ammonia, or urea may degrade, and the amino acids naturally reduce ammonia.

While the use of the presently disclosed and claimed inventive concept(s) is described in particular for use with diagnostic reagents (such as but not limited to, calibration and quality control reagents), it is to be understood that the scope of the presently disclosed and claimed inventive concept(s) encompasses use with any aqueous urea-containing solutions in which stabilization of the pH thereof is desired.

In one embodiment, the presently disclosed and claimed inventive concept(s) is directed to a composition comprising an aqueous quality control or calibration reagent disposed in a closed system (such as but not limited to, a zero head space closed system). The composition includes urea, at least one buffer, and at least one amino acid-containing composition. The at least one amino acid-containing composition has one or more available primary or secondary amine(s) and is present in a sufficient amount to stabilize the pH of the aqueous quality control or calibration reagent upon storage of the composition.

The term "closed system" refers to a sealed or otherwise contained system which does not permit the reagent contained therein to react with its environment. In a "zero head space closed system," the reagent disposed in a container maximizes the volume of the container as much as possible, so that the volume available for gasses to be trapped within the closed system is minimized as much as possible.

In certain embodiments, the pH of the aqueous quality control or calibration reagent is in a range of from about 6 to about 8, and the pH of the reagent varies by +/−1.0 or less of the original pH following storage thereof, such as +/−0.5 or less of the original pH, +/−0.2 or less of the original pH, +/−0.1 or less of the original pH, +/−0.05 or less of the original pH, +/−0.02 or less of the original pH, +/−0.01 or less of the original pH, or +/−0.005 or less of the original pH.

The at least one amino acid-containing composition may include any amino acid-containing composition known in the art or otherwise contemplated herein that is capable of functioning in accordance with the presently disclosed and claimed inventive concept(s). For example but not by way of limitation, the amino acid-containing composition may include single amino acids, small peptides, longer polypeptides and/or full-length proteins; the only requirement is that the amino acid-containing composition has at least one primary and/or secondary amine that provides available site(s) to react with intermediate urea degradation products (such as but not limited to, cyanates). Many amino acids and combinations of amino acids help control urea degradation in solution. Non-limiting examples of amino acids that may be present in the amino acid-containing composition include, but are not limited to, lysine, arginine, ornithine, taurine, histidine, asparagine, threonine, as well as combinations and derivatives thereof. In certain embodiments, the pKa of at least one amino acid carboxyl group in the at least one amino acid-containing composition is in a range of from about 1.5 to about 2.7.

The pH stability described herein above may be observed under a variety of storage conditions. Non-limiting examples of storage conditions include: storage for at least six months at a temperature in a range of from 1° C. to 8° C.; storage for at least six weeks at a temperature in a range of from 9° C. to 17° C.; storage for at least four weeks at a temperature in a range of from 18° C. to 32° C.; storage for at least one week at a temperature in a range of from 33° C. to 44° C.; and storage for at least 24 hours at a temperature in a range of from 45° C. to 50° C. Other non-limiting examples of storage conditions include: storage for at least one year or at least two years at a temperature in a range of from 1° C. to 8° C.; storage for at least three months, six months, nine months, or one year at a temperature in a range of from 9° C. to 17° C.; storage for at least two months, three months, four months, five months, six months, seven months, eight months, nine months, ten months, eleven months, or one year at a temperature in a range of from 18° C. to 32° C.; (d) storage for at least two weeks, three weeks, or four weeks at a temperature in a range of from 33° C. to 44° C.; and storage for at least 48 hours, 72 hours, or five days at a temperature in a range of from 45° C. to 50° C.

In certain embodiments, the at least one amino acid-containing composition may be present in an amount sufficient to control the generation of urea degradation products that may affect the reagent's pH stability. For example but not by way of limitation, the at least one amino acid-containing composition may be present in an amount sufficient to substantially reduce the formation of ammonia and/or carbon dioxide in the aqueous quality control or calibration reagent following storage of the composition. For example but not by way of limitation, the formation of ammonia may be reduced by at least 5%, or at least 10%, or at least 15%, or at least 20% following storage of the composition. In another non-limiting example, a carbon dioxide concentration of less than 150 mm Hg+/−3% is observed following storage of the composition.

Urea may be present in the composition at any desired concentration that (1) allows the aqueous calibration or quality control reagent to function as desired, and (2) allows the pH thereof to be controlled via the presence of the at least one amino acid-containing composition. For example but not by way of limitation, urea may be present in the aqueous reagent at a concentration in a range of from about 0.1 mM to about 150 mM, or a range of from about 1.5 mM to about 55 mM, or a range of from about 10 mM to about 40 mM, or a range of from about 30 mM to about 40 mM.

In addition, the ratio of urea to the at least one amino acid-containing composition may be any desired ratio that (1) allows the aqueous calibration or quality control reagent to function as desired, and (2) allows the pH thereof to be controlled via the presence of the at least one amino acid-containing composition. For example but not by way of limitation, the ratio of urea to the at least one amino acid-containing composition may be in a range of from about 0.1:1 to about 100:1, or in a range of from about 0.5:1 to about 10:1, or in a range of from about 1:1 to about 5:1, or in a range of from about 3:1 to about 4:1. In certain embodiments, the ratio of urea to the at least one amino acid-containing composition is about 3.57:1.

The buffer present in the composition may be any buffer known in the art or otherwise contemplated herein for use in accordance with the presently disclosed and claimed inventive concept(s). Non-limiting examples of buffers that may be used in accordance with the presently disclosed and claimed inventive concept(s) include MOPS, MES, ADA, PIPES, ACES, Cholamine chloride, BES, TES, HEPES, Acetamidoglycine, Tricine, Glycinamide, Bicine, phosphate, and combinations and derivatives thereof. In certain embodiments, the at least one amino acid-containing composition may also serve as the at least one buffer present in the composition.

The aqueous quality control or calibration reagent may be utilized with any sensors known in the art or otherwise contemplated herein, such as but not limited to, a Blood Urea Nitrogen (BUN) sensor, or a creatinine sensor.

The presently disclosed and claimed inventive concept(s) further includes kits containing any of the embodiments of compositions described herein above; the kit may contain at least one of the compositions described herein above or any combination of any of the embodiments of compositions described herein above. For example but not by way of limitation, the kit may contain one or more compositions comprising an aqueous calibration reagent as described herein above and one or more compositions comprising an aqueous quality control reagent as described herein above. In addition, the kit may further contain other components/reagent(s) that could be utilized with the compositions described herein above. The nature of these additional components/reagent(s) will depend upon the particular assay format, and identification thereof is well within the skill of one of ordinary skill in the art. A non-limiting example of another component/reagent that may be provided in a kit containing at least one of the compositions described herein above is a wash solution.

The compositions/components/reagents may each be disposed in separate closed system containers/compartments, or various components/reagents can be combined in one or more closed system containers/compartments, depending on the cross-reactivity and stability of the compositions/components/reagents. The kit can further include other separately packaged reagents for conducting an assay. In addition, the kit may include a microfluidics device in which the components/reagents are disposed.

The relative amounts of the various compositions/components/reagents in the kits can vary widely to provide for concentrations of the compositions/components/reagents that substantially optimize the reactions that need to occur during the assay methods and further to optimize substantially the sensitivity of an assay. The kit can further include a set of written instructions explaining how to use the kit. A kit of this nature can be used in any of the methods described or otherwise contemplated herein.

The presently disclosed and claimed inventive concept(s) is also directed to a method of stabilizing the pH of an aqueous quality control or calibration reagent as described herein above. The method includes disposing at least one amino acid-containing composition (as described in detail herein above) into an aqueous quality control or calibration reagent (as described herein above), whereby control of the pH of the reagent is provided by the presence of the at least one amino acid-containing composition therein.

EXAMPLES

Examples are provided herein below. However, the presently disclosed and claimed inventive concept(s) is to be understood to not be limited in its application to the specific experimentation, results and laboratory procedures described in the Examples. Rather, the Examples are simply provided as one of various embodiments and are meant to be exemplary, not exhaustive.

Example 1

In the present Example, a multianalyte reference solution (200 G Cal) at pH 6.8 and 10 mg/dL BUN (Blood Urea Nitrogen) with tonometered carbon dioxide and oxygen was disposed into a zero headspace pouch and tested. The formulation targets of these reagents are shown in Table 1.

TABLE 1

| Parameter | Unit | Target |
|---|---|---|
| pH | | 6.7-6.9 |
| $Na^+$ | mM | 110-120 |
| $K^+$ | mM | 3.8-4.2 |
| $Ca^{+2}$ | mM | 1.15-1.35 |
| $Cl^-$ | mM | 92-102 |
| Glucose | mg/dL | 170-190 |
| BUN | mg/dL | 8-12 |
| Creatinine | mg/dL | 0.8-1.2 |

Reagent samples had been stored at 25° C. for 8 weeks, 35° C. for 6 weeks, 45° C. for three weeks, 50° C. for three weeks, or 55° C. for 3 weeks, respectively, and were then stored at 4° C. for 1 year prior to being tested. Solutions were the control (normal formulation), and 10 mM Lysine. The lysine was significantly more stable (~¼ the loss) for pH than the control.

FIG. 1 depicts the pH variation seen at 35° C. over various storage periods. A pH shift of almost 0.014 was observed after four weeks at 35° C. in the 200 Cal reagent in the absence of amino acid, whereas this pH shift was reduced to less than 0.006 (i.e., greater than 50% reduction observed) in the presence of lysine.

The observed change in pH at 4° C. versus 45° C. following storage for 4 weeks was −0.045 for the control and −0.008 for the lysine-containing reagent (which is an acceptable uselife specification). This represents a significant improvement in pH stability.

Example 2

In this Example, a multianalyte reference solution containing urea and 50 mM MOPS Buffer (RCx reagent) at pH 7.4 was dispensed into a zero headspace pouch and stored for four weeks at various temperatures in the absence or presence of lysine, threonine, arginine, ornithine, or a combination of arginine-ornithine. The formulation targets of these various reagents are shown in Table 2.

TABLE 2

| Parameter | Unit | Target |
|---|---|---|
| pH | | 7.3-7.5 |
| $Na^+$ | mM | 110-130 |

TABLE 2-continued

| Parameter | Unit | Target |
|---|---|---|
| $K^+$ | mM | 7.8-8.2 |
| $Ca^{+2}$ | mM | 0.58-0.69 |
| $Cl^-$ | mM | 68-72 |
| BUN | mg/dL | 38-43 |
| Creatinine | mg/dL | 4.5-6.0 |

Figure 2:
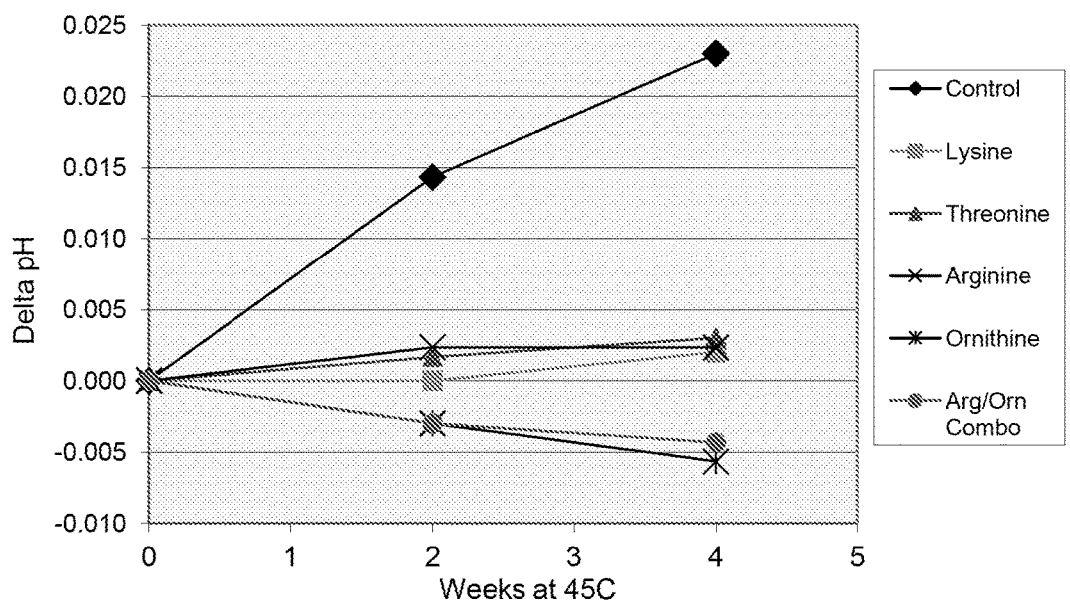
FIG. 2 graphically depicts the pH shift observed in the urea-containing RCx reagent in the presence or absence of various amino acids upon storage at 45° C. for various periods of time.
Figure 3:
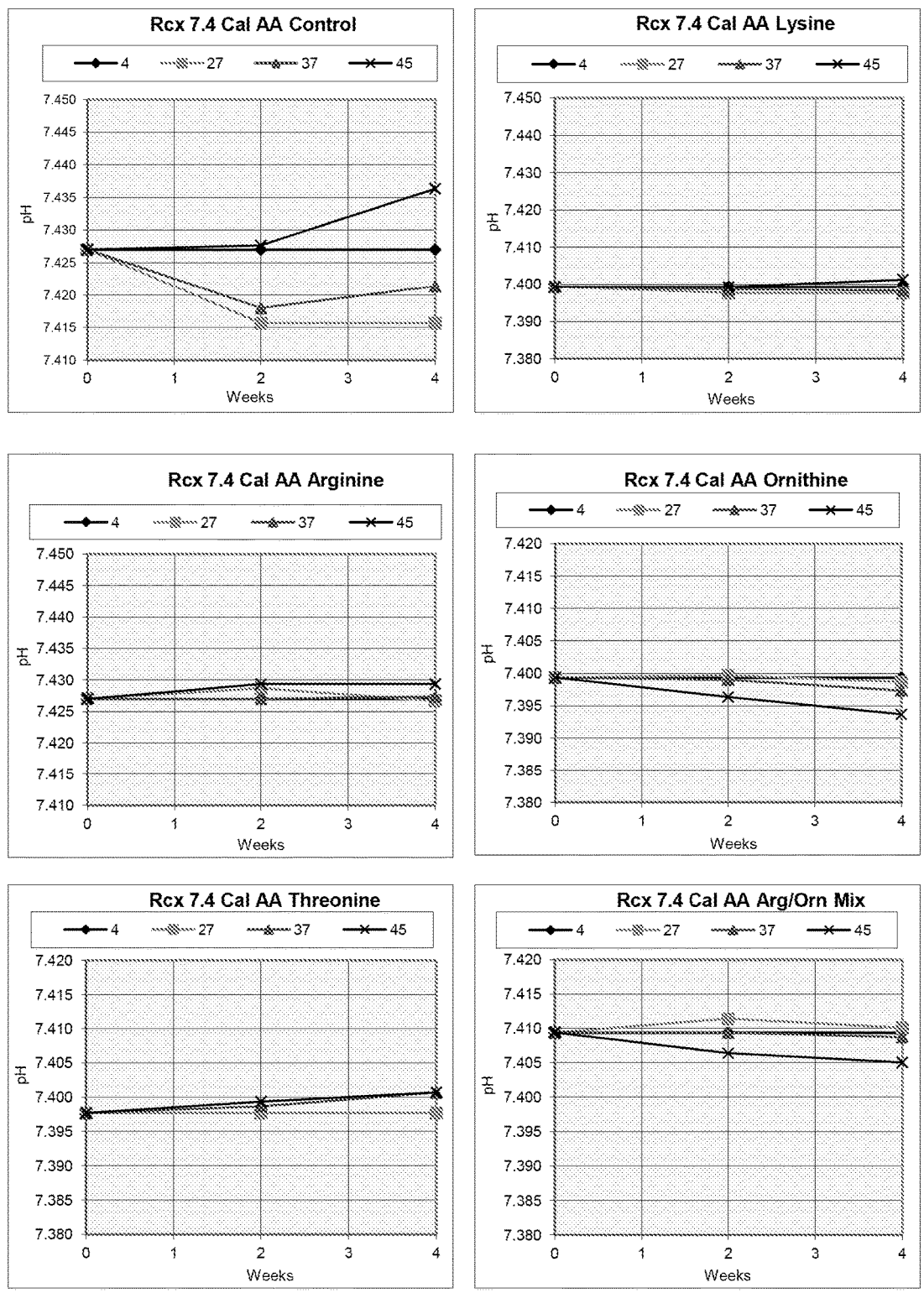
FIG. 3 graphically depicts the variations in pH levels observed at various temperatures and periods of time for the RCx reagent in the presence or absence of various amino acids.
Figure 4:
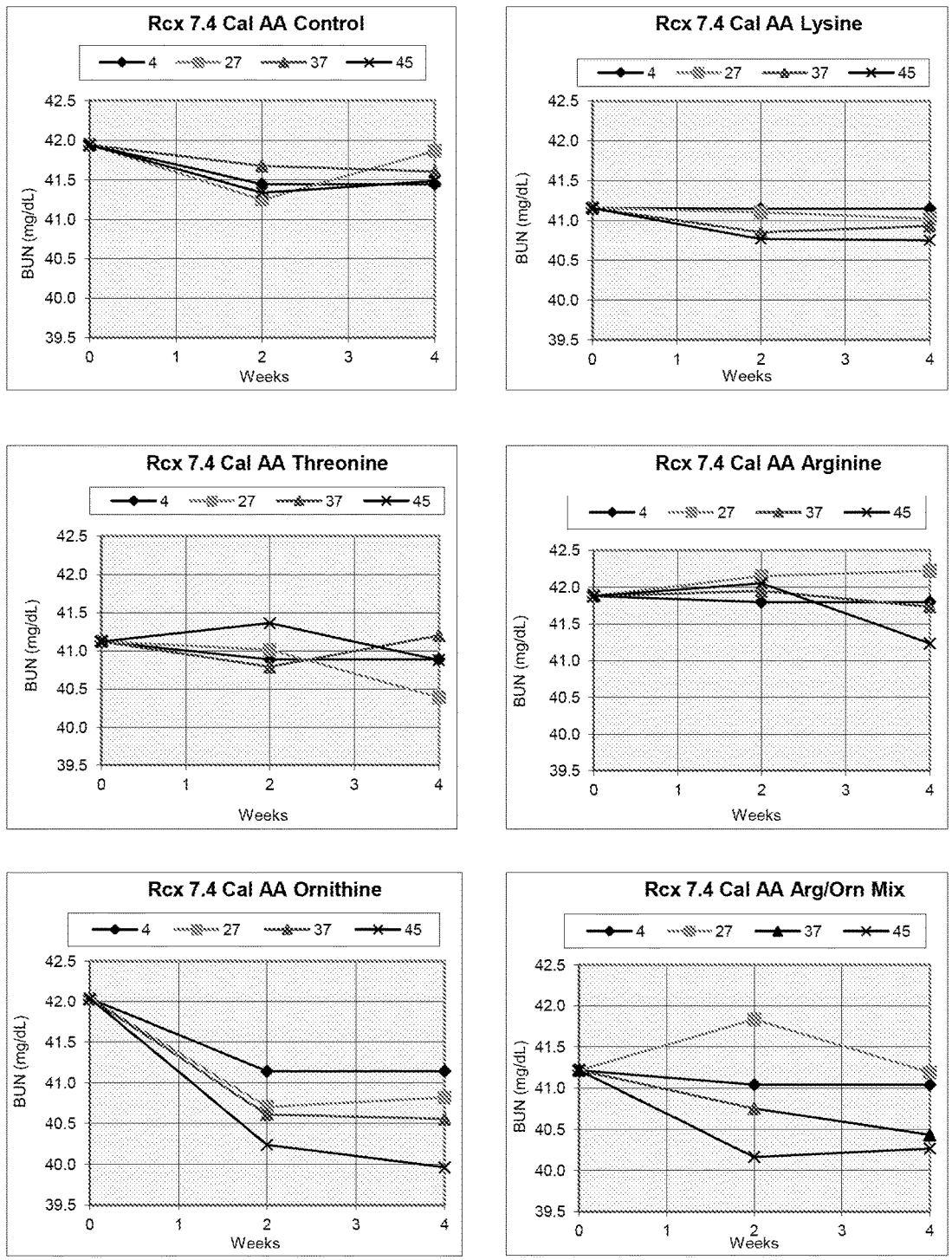
FIG. 4 graphically depicts the variations in BUN concentrations observed at various temperatures and periods of time for the RCx reagent in the presence or absence of various amino acids.
Figure 5:
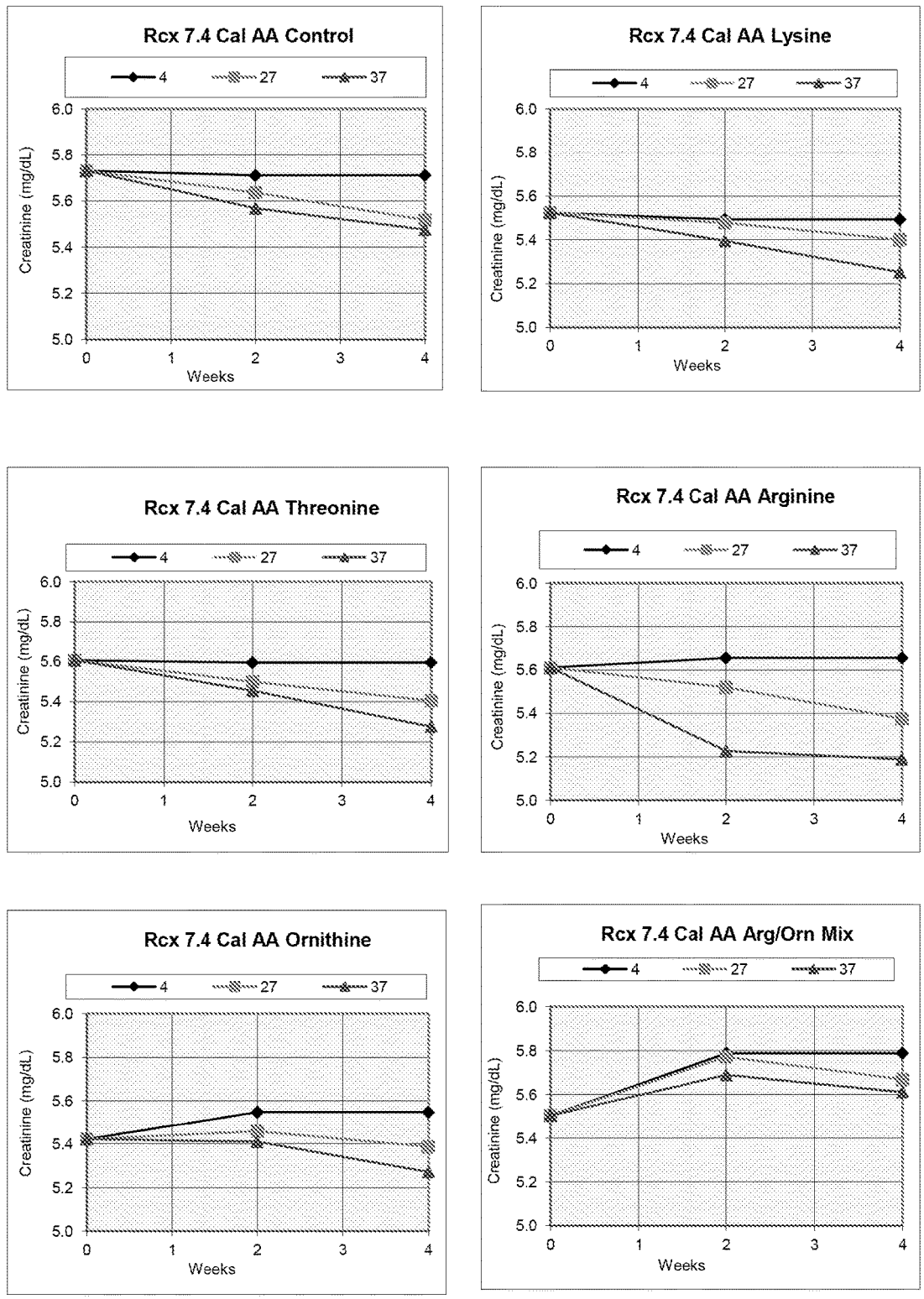
FIG. 5 graphically depicts the variation in creatinine concentrations observed at various temperatures and periods of time for the RCx reagent in the presence or absence of various amino acids.
Figure 6:
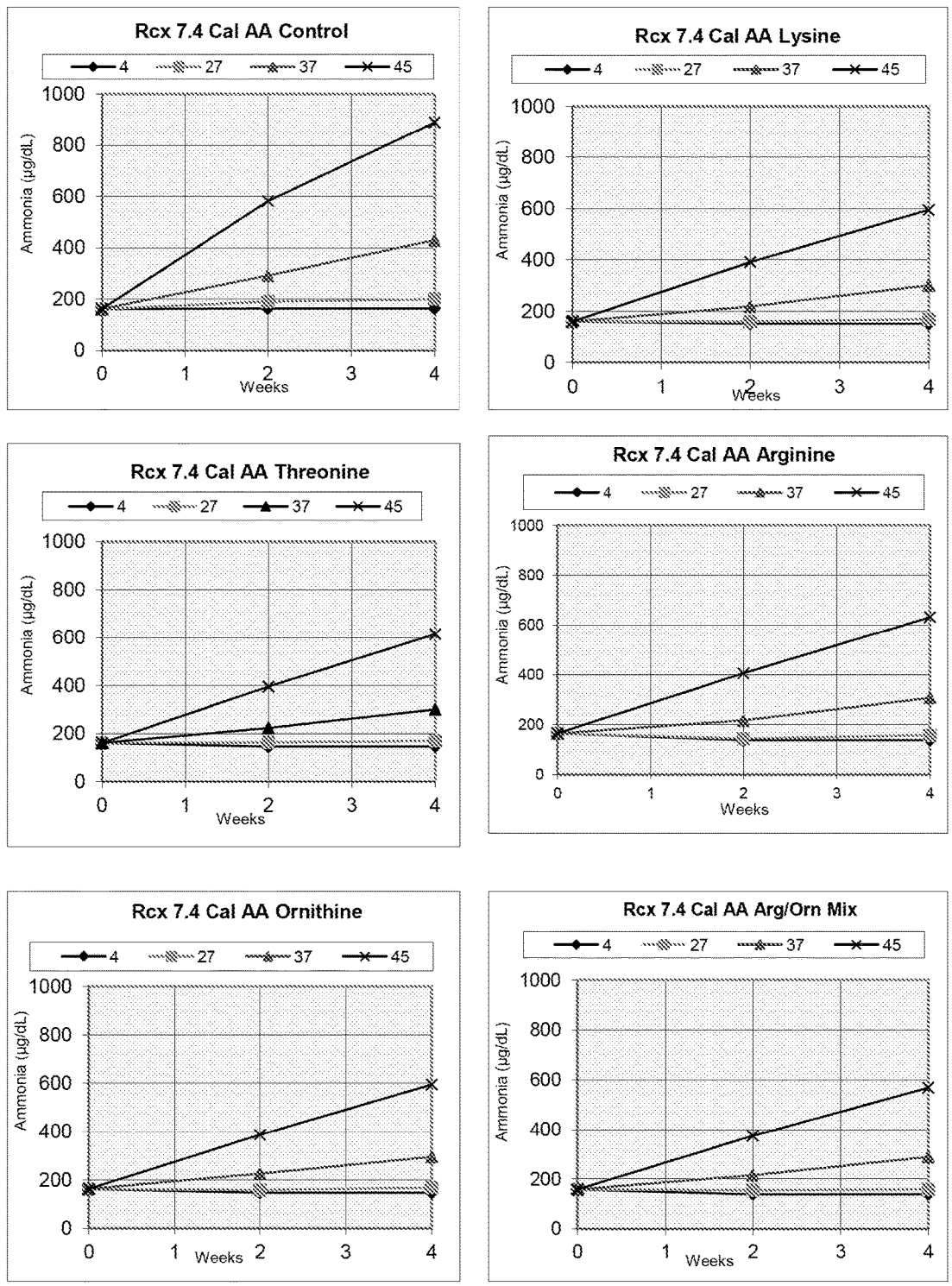
FIG. 6 graphically depicts the variation in ammonia concentrations observed at various temperatures and periods of time for the RCx reagent in the presence or absence of various amino acids.

FIG. 2 illustrates the pH variation observed for the various reagents upon storage at 45° C. for up to four weeks. A pH increase of 0.023 was observed in the RCx reagent in the absence of amino acids; however, the presence of 10 mM lysine, 10 mM arginine, or 10 mM threonine in the RCx reagent reduced this pH increase to only ~0.003. The presence of 10 mM ornithine or 5 mM arginine/10 mM ornithine resulted in a decrease in the pH to ~−0.005 of the original pH of the RCx reagent.

FIGS. 3-6 depict the pH levels and BUN, creatinine, and ammonia concentrations, respectively, that were observed in the RCx reagents in the presence and absence of the various amino acids upon storage at various temperatures and for 1 to 4 weeks of storage. From these Figures, it is evident that the addition of amino acids reduced ammonia formation and significantly improved stability.

Figure 7:
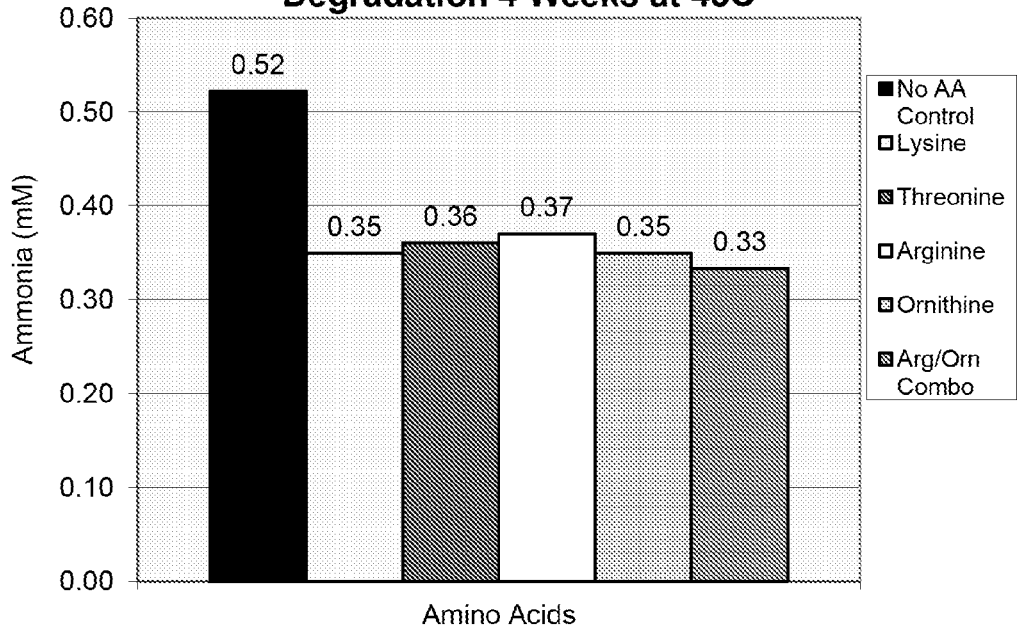
FIG. 7 illustrates the levels of ammonia generation observed following storage for four weeks at 45° C. in the RCx reagent in the presence or absence of various amino acids.

An increase in ammonia concentration to 0.52 mM was observed in the absence of amino acid (FIG. 7), and this increase was reduced to a level of 0.33-0.37 mM in the presence of the various amino acids. This represents a 27-37% reduction in the amount of ammonia generated following storage for four weeks at 45° C.

Example 3

In this Example, the RCx reagent from Example 2 at pH 7.3 and 50 mM MOPS Buffer was tested in the presence of different amino acids. The formulation targets of these various reagents, which included no amino acid or taurine, histidine, asparagine, niacinamide, or nicotinic acid, are shown in Table 3.

TABLE 3

| Parameter | Unit | Target |
|---|---|---|
| pH | | 7.3-7.5 |
| $Na^+$ | mM | 110-130 |
| $K^+$ | mM | 7.8-8.2 |
| $Ca^{+2}$ | mM | 0.58-0.69 |
| $Cl^-$ | mM | 68-72 |
| BUN | mg/dL | 38-43 |
| Creatinine | mg/dL | 4.5-6.0 |

Figure 8:
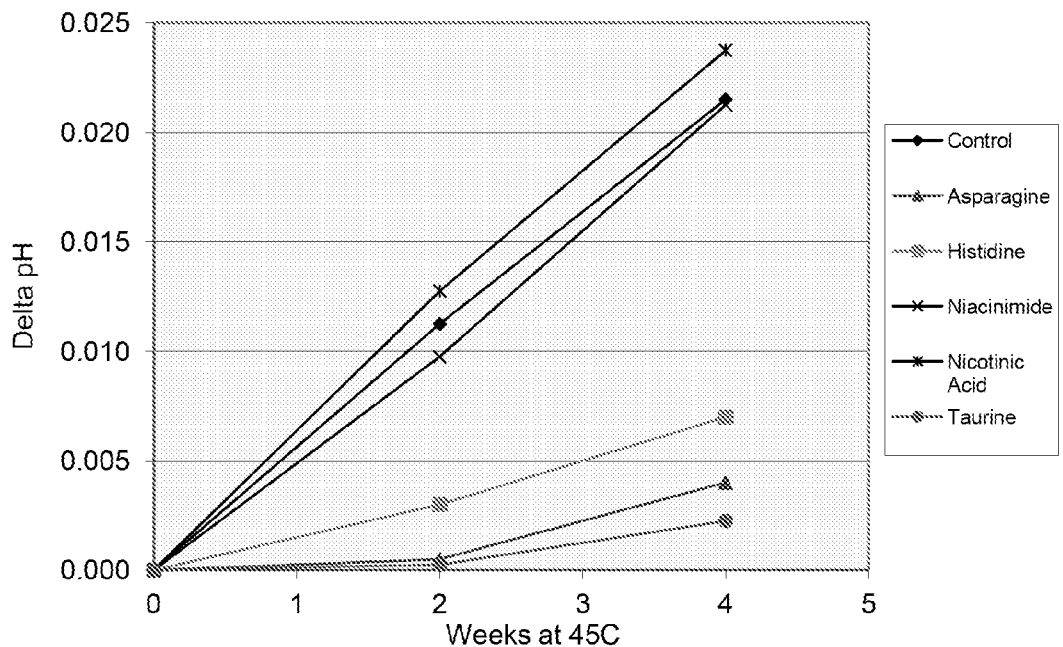
FIG. 8 graphically depicts the pH shift observed in Reagent C in the presence or absence of various amino acids upon storage for four weeks at 45° C.
Figure 9:
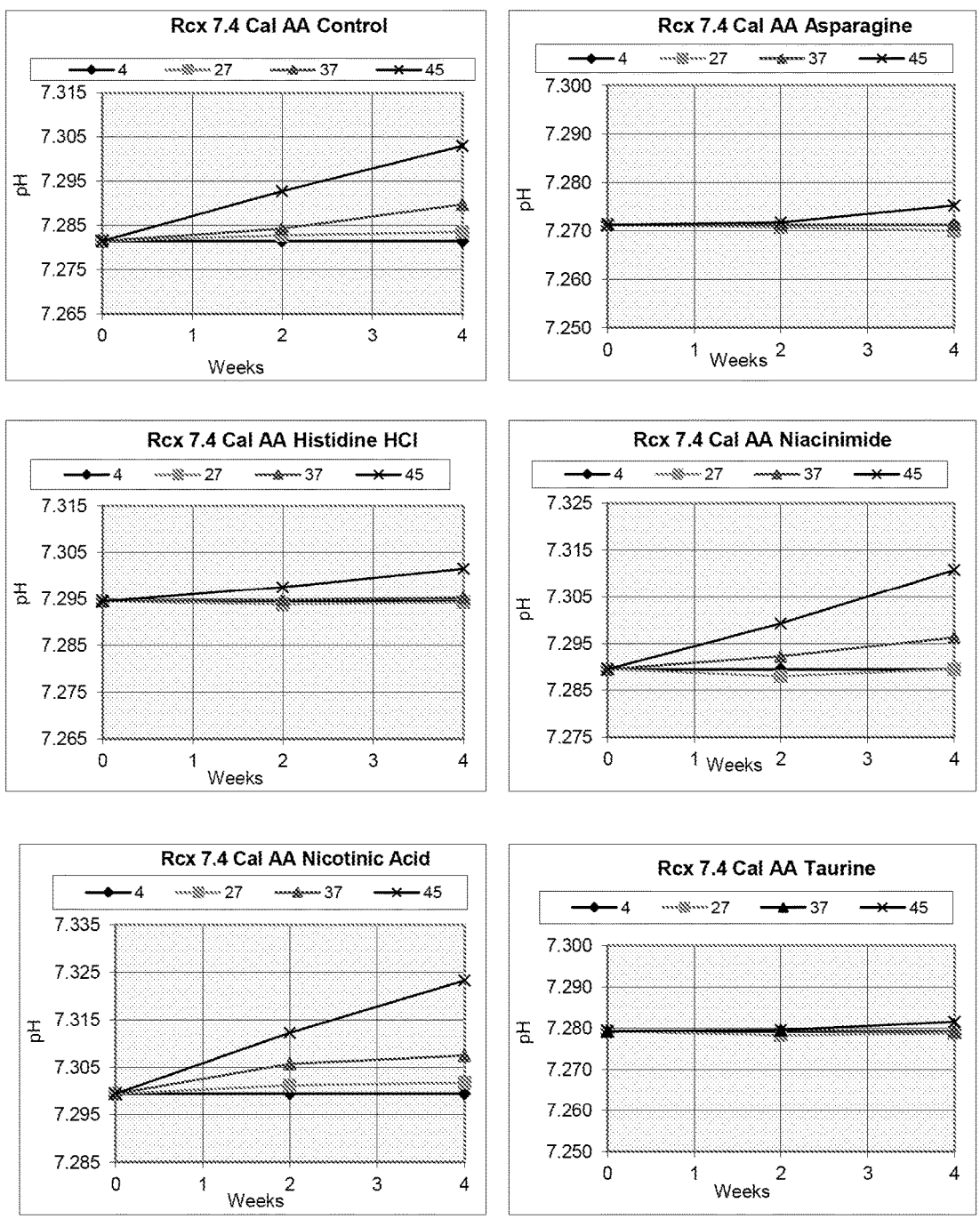
FIG. 9 graphically depicts the pH shifts observed in the urea-containing RCx 7.4 Cal AA reagent in the presence or absence of various amino acids upon storage at various temperatures and periods of time.
Figure 10:
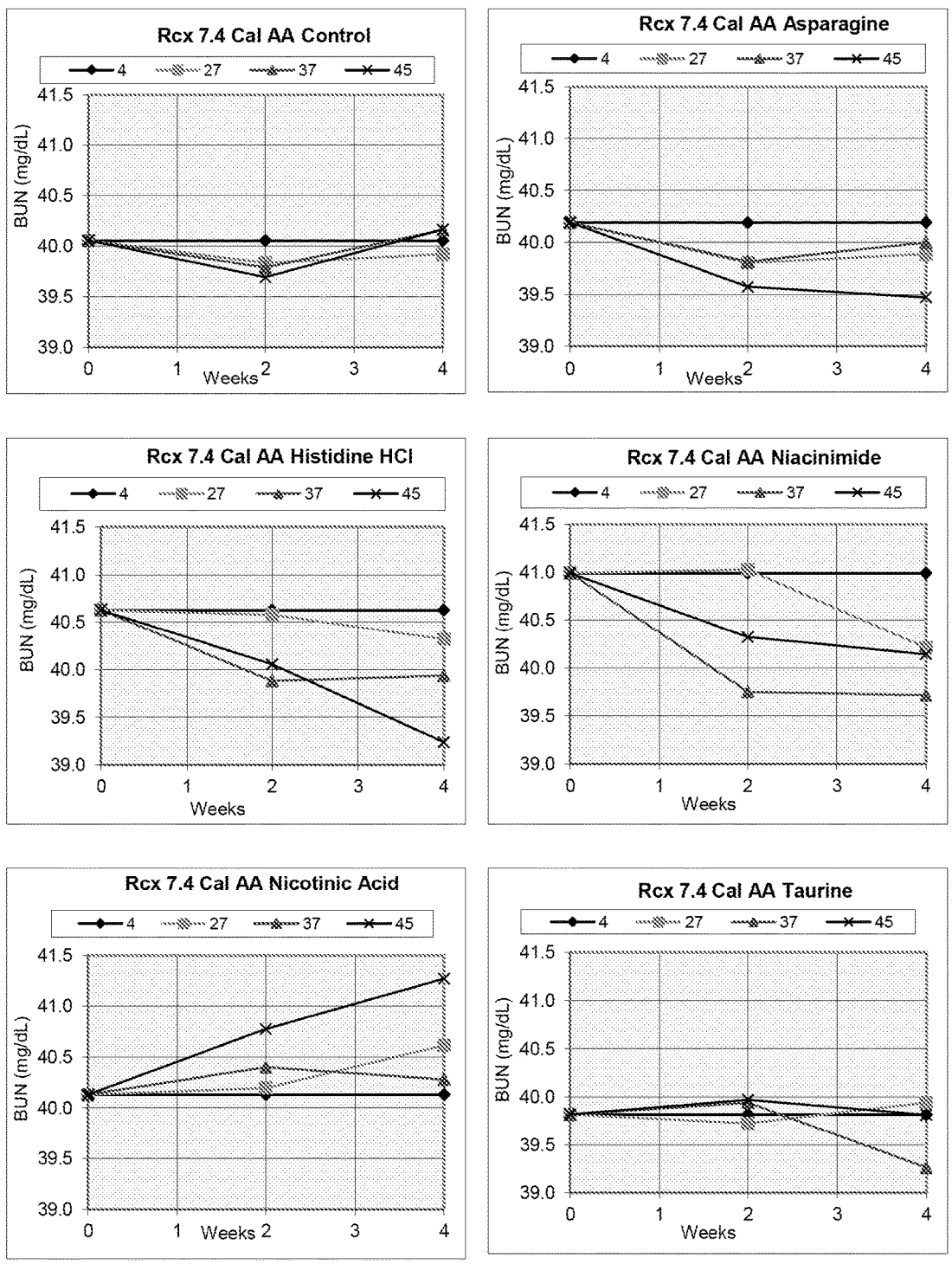
FIG. 10 graphically depicts the variations in BUN concentrations observed at various temperatures and periods of time for the RCx 7.4 Cal AA reagent in the presence or absence of various amino acids.
Figure 11:
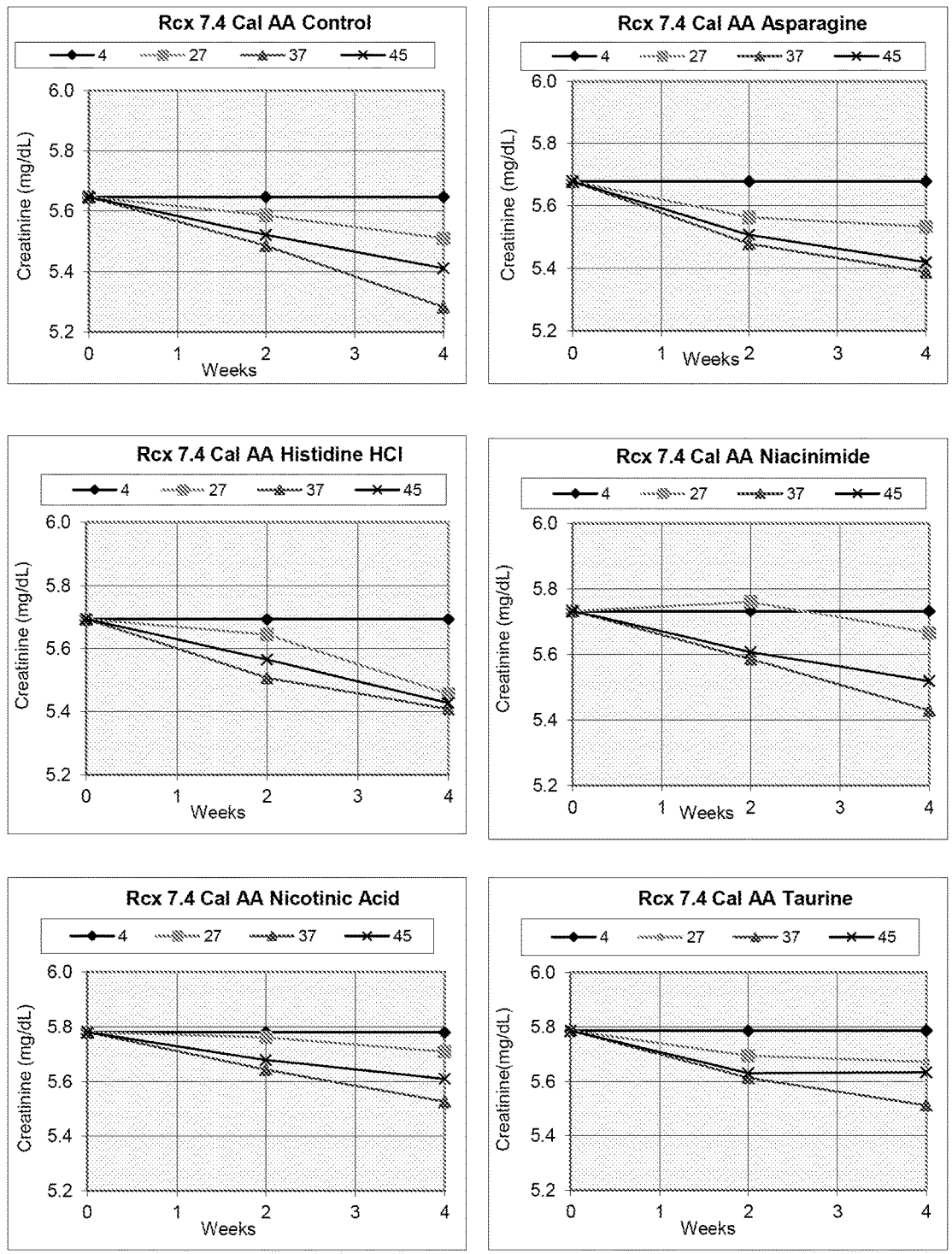
FIG. 11 graphically depicts the variation in creatinine concentrations observed at various temperatures and periods of time for the RCx 7.4 Cal AA reagent in the presence or absence of various amino acids.

FIG. 8 illustrates the pH variation observed for the various reagents upon storage at 45° C. for up to four weeks. A pH increase of 0.023 was observed in the RCx reagent in the absence of amino acids as well as in the presence of 10 mM niacinamide, and a greater pH increase was observed in the presence of 10 mM nicotinic acid. However, the presence of 10 mM histidine, 10 mM asparagine, or 10 mM taurine in the RCx reagent greatly reduced the shift in pH observed (to ~0.007, ~0.004, and ~0.0025, respectively).

FIGS. 9-11 and 13 depict the pH levels and BUN, creatinine, and ammonia concentrations, respectively, that were observed in the RCx reagent in the presence and absence of the various amino acids upon storage at various temperatures and for 1 to 4 weeks of storage. From these Figures, it is evident the presence of amino acids significantly improved the stability of pH by limiting the generation of ammonia.

Figure 12:
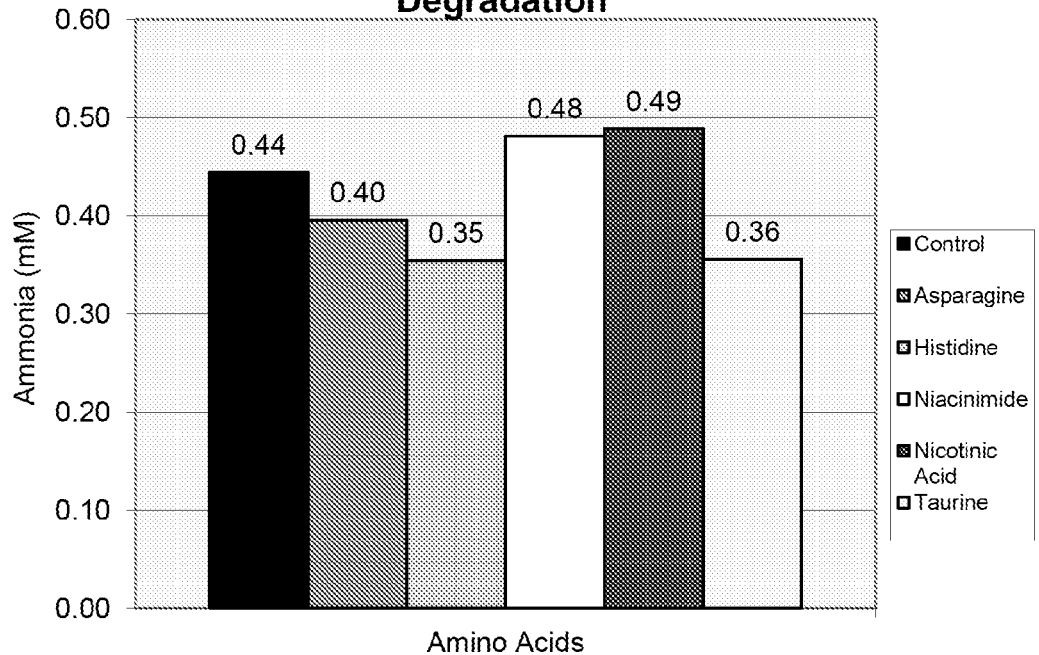
FIG. 12 illustrates the levels of ammonia generation observed following storage for four weeks at 45° C. in the RCx reagent in the presence or absence of various amino acids.

An increase in ammonia concentration to 0.44 mM was observed in the RCx reagent in the absence of amino acid following storage for four weeks at 45° C. (FIG. 12), and a greater increase in ammonia concentration was observed in the presence of niacinimide and nicotinic acid (0.48 and 0.49 mM, respectively). However, the presence of the other amino acids resulted in a decrease in the levels of ammonia generated under these storage conditions, with 0.40 mM observed for the reagent containing asparagine, 0.36 mM observed for the reagent containing taurine, and 0.35 mM observed for the reagent containing histidine. This represents a 9-21% reduction in the amount of ammonia generated following storage for four weeks at 45° C.

Example 4

This Example illustrates the results obtained with the multianalyte reference solution containing urea (Zero Cal reagent) tonometered with carbon dioxide at pH 7.4 in the presence or absence of lysine and dispensed into zero headspace pouches. The formulation targets of these reagents are shown in Table 4.

TABLE 4

| Parameter | Unit | Target |
|---|---|---|
| pH | | 7.3-7.5 |
| $pCO_2$ | mmHg | 65-85 |
| $Na^+$ | mM | 150-170 |
| $K^+$ | mM | 7.8-8.2 |
| $Ca^{+2}$ | mM | 0.58-0.69 |
| $Cl^-$ | mM | 68-72 |
| BUN | mg/dL | 35-45 |

Figure 14:
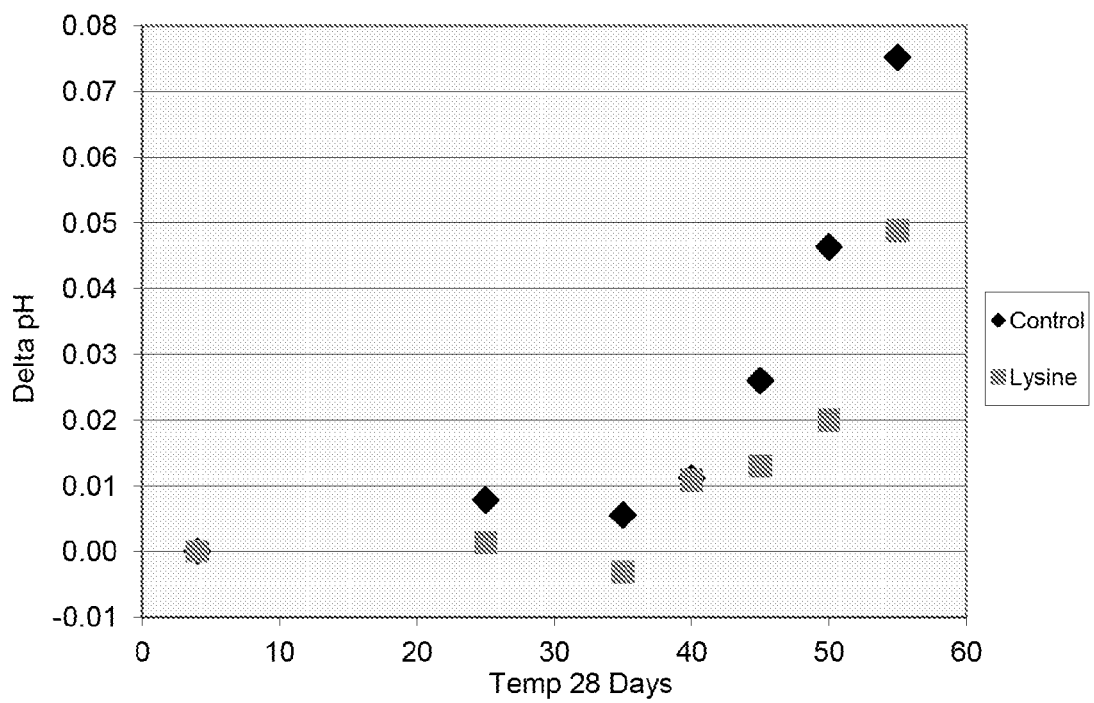
FIG. 14 graphically depicts the pH shifts observed in Zero Cal reagent in the presence or absence of lysine upon storage for 28 days at various temperatures.
Figure 13:
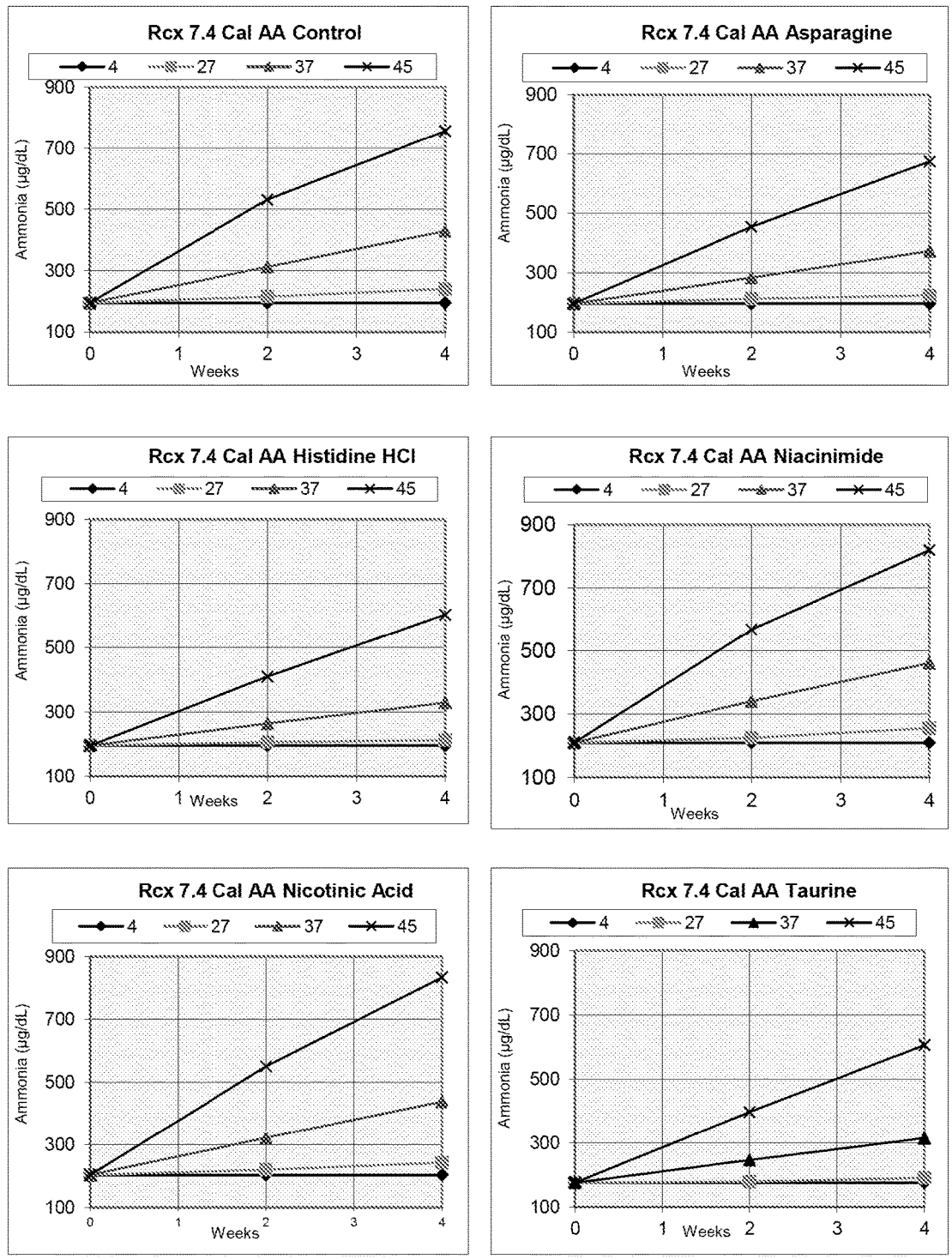
FIG. 13 graphically depicts the variation in ammonia concentrations observed at various temperatures and periods of time for the RCx 7.4 Cal AA reagent in the presence or absence of various amino acids.

FIG. 14 depicts the pH variation seen at various temperatures upon storage for 28 days. A pH shift of ~0.045 was observed at 50° C. in the Zero Cal reagent in the absence of amino acid, whereas this pH shift was reduced to less than 0.02 (i.e., greater than 50% reduction observed) in the presence of 10 mM lysine. An approximately 50% reduction in the pH shift was also observed at 25° C., 35° C., and 45° C.

Example 5

In the present Example, ammonia regulation and pH stability of a buffered calibration solution containing 40 mM MOPS and 100 mg/dL BUN (35.7 mM urea) targeting pH 6.8 and tonometered with carbon dioxide and oxygen was dispensed into zero headspace pouches and tested at 30° C. for various storage periods in the presence or absence of 10 mM amino acid (arginine or ornithine). The formulation targets of these reagents are shown in Table 5.

TABLE 5

| Parameter | Unit | Target |
|---|---|---|
| pH | | 6.7-7.0 |
| $Na^+$ | mM | 20-40 |
| $K^+$ | mM | 3.8-4.2 |
| $Ca^{+2}$ | mM | 1.15-1.35 |
| $Mg^{+2}$ | mM | 0.80-1.00 |
| BUN | mg/dL | 90-105 |
| Creatinine | mg/dL | 9.0-11.0 |

Figure 15:
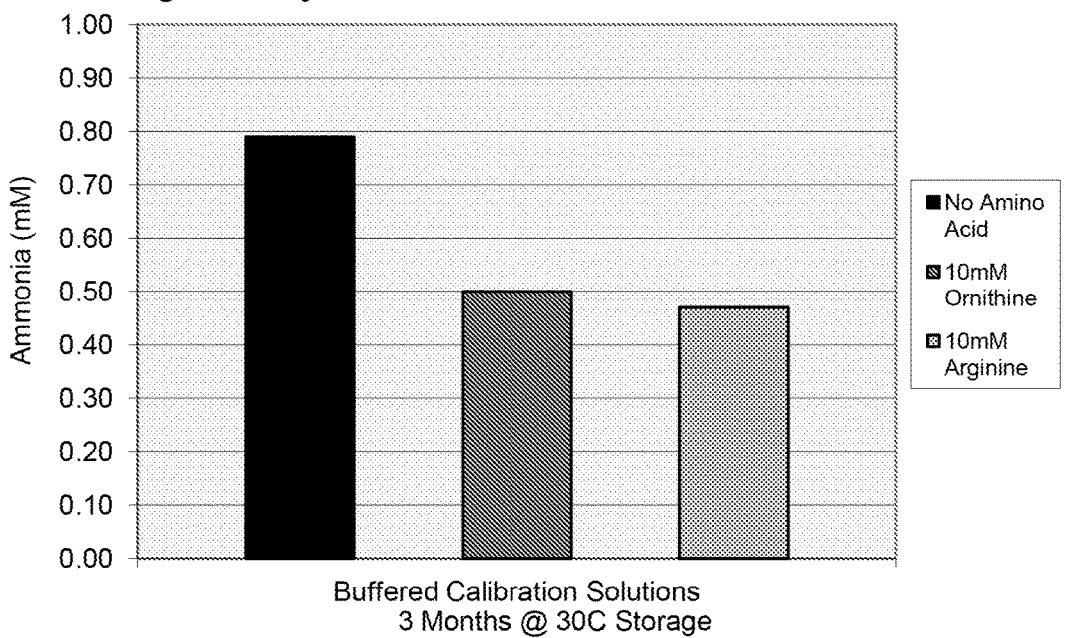
FIG. 15 illustrates the levels of ammonia generation observed following storage for three months at 30° C. for various buffered calibration solutions containing 100 mg/dL BUN (Blood Urea Nitrogen), either in the presence or absence of ornithine or arginine.
Figure 16:
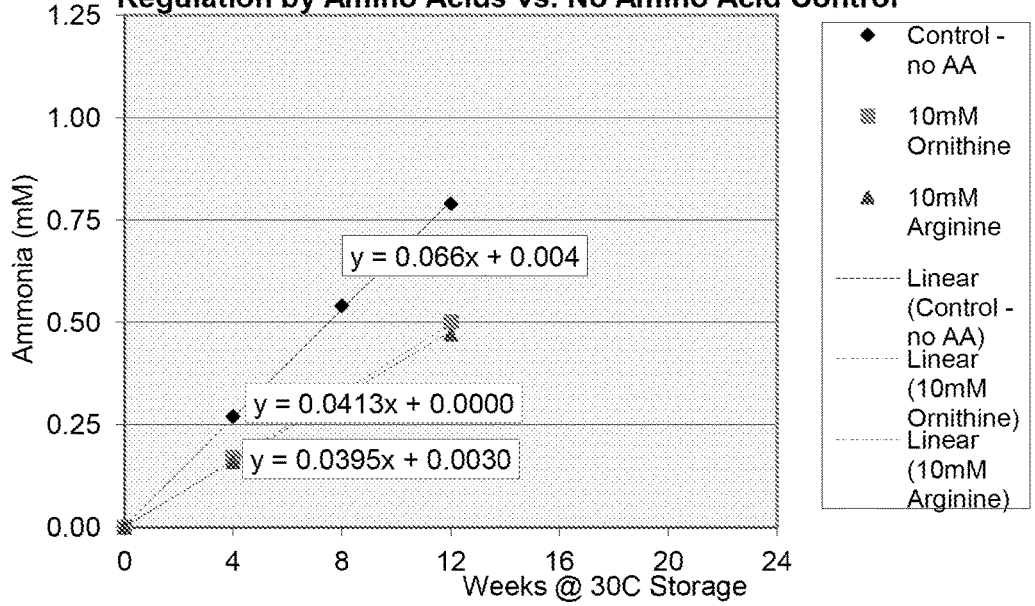
FIG. 16 graphically depicts the levels of ammonia generation observed following storage for various time periods at 30° C. for various buffered calibration solutions containing 100 mg/dL BUN, either in the presence or absence of ornithine or arginine.

FIGS. 15-16 illustrate the effects of arginine and ornithine on ammonia regulation of the buffered calibration solution. An increase in ammonia concentration to 0.78 mM was observed in the solution in the absence of amino acid following storage for three months (FIG. 15), and this concentration was reduced by 36% and 41% in the presence of ornithine or arginine, respectively (i.e., to 0.50 and 0.46 mM). FIG. 16 illustrates the increase in ammonia concentration observed upon storage of the solution for up to 12 weeks in the presence or absence of ornithine or arginine.

Figure 17:
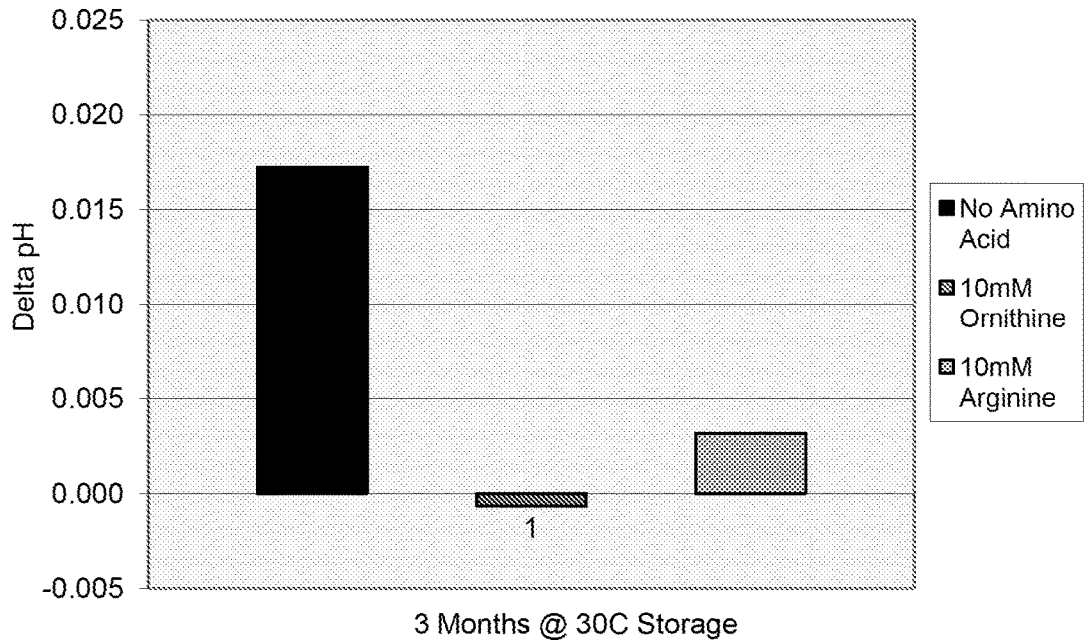
FIG. 17 illustrates the variations in pH observed following storage for three months at 30° C. for various buffered calibration solutions containing 100 mg/dL BUN, either in the presence or absence of ornithine or arginine.
Figure 18:
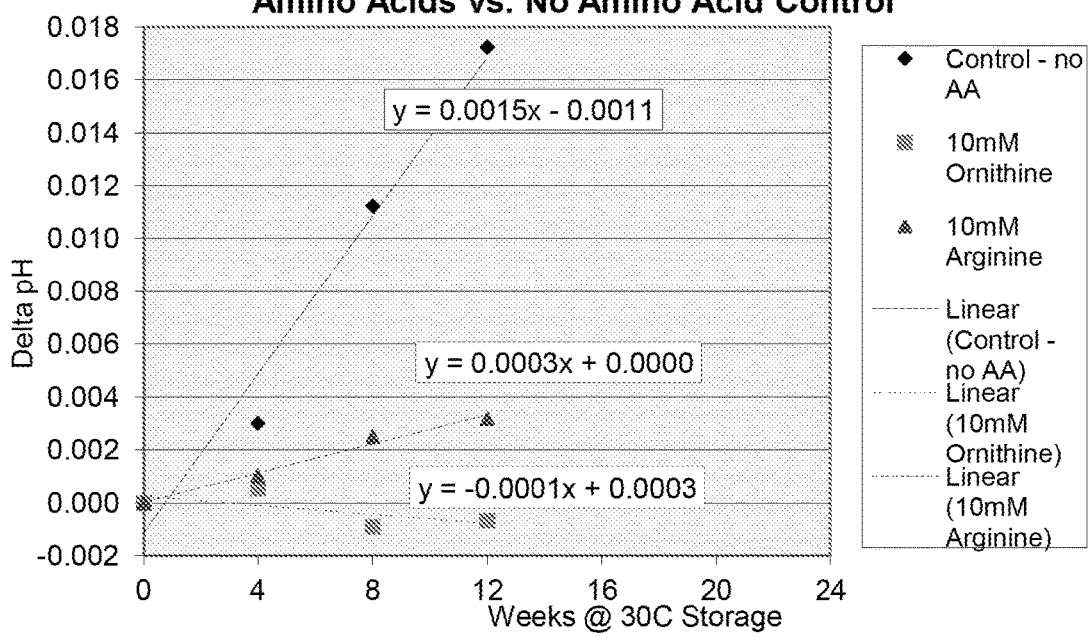
FIG. 18 graphically depicts the levels of ammonia generation observed following storage for various time periods at 30° C. for various buffered calibration solutions containing 100 mg/dL BUN, either in the presence or absence of ornithine or arginine.

FIGS. 17-18 illustrate the effects of arginine and ornithine on stabilization of the pH of the buffered calibration solution. A pH shift of 0.017 was observed in the solution in the absence of amino acid following storage for three months (FIG. 17), and this shift was dramatically reduced upon the addition of either arginine or ornithine to the buffered calibration solution (to a −0.001 shift in the presence of ornithine and a 0.003 shift in the presence of arginine). This represents an approximately 85% reduction in the pH variation seen in the absence of amino acid. FIG. 18 illustrates the pH variation observed upon storage of the solution for up to 12 weeks in the presence or absence of ornithine or arginine.

Example 6

In the present Example, the percent increase in ammonia in a urea-containing buffered calibration was calculated following storage for up to 16 weeks at 30° C. at 60 mg/dL BUN (21.4 mM urea). The formulation targets of these reagents are shown in Table 6.

TABLE 6

| Parameter | Unit | Target |
| --- | --- | --- |
| pH | | 6.7-7.0 |
| $Na^+$ | mM | 20-40 |
| $K^+$ | mM | 3.8-4.2 |
| $Ca^{+2}$ | mM | 1.15-1.35 |
| $Mg^{+2}$ | mM | 0.80-1.00 |
| BUN | mg/dL | 55-65 |
| Creatinine | mg/dL | 9.0-11.0 |

Figure 19:
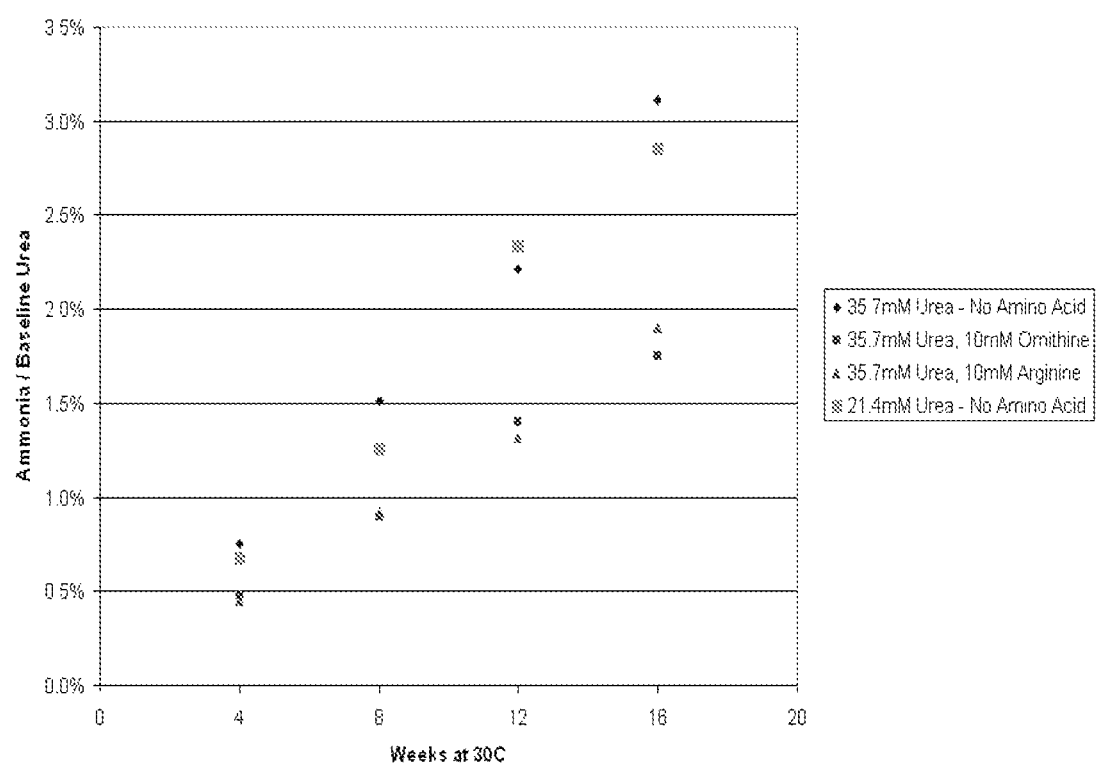
FIG. 19 graphically depicts the percent ammonia increase (in relation to original urea concentration) observed at various time periods at 30° C. for a buffered calibration solution containing urea at two different concentrations, either in the presence or absence of ornithine or arginine.

At 16 weeks, the percent ammonia increase in relation to the original urea concentration was 2.85% for 21.4 mM urea and 3.11% for 35.7 mM urea solution in Example 5 with no amino acid added. At 35.7 mM urea and 10 mM amino acid concentrations in Example 5, the percent ammonia increase in relation to the original urea concentration was reduced to 1.90% for arginine and 1.75% for ornithine. This indicates that urea in solution directly leads to formation of ammonia relative to the amount of urea added to the solution, and the formation of ammonia can be reduced by the addition of amino acids. FIG. 19 illustrates this relationship.

Thus, in accordance with the presently disclosed and claimed inventive concept(s), there has been provided a mechanism of controlling/stabilizing pH in aqueous urea-containing compositions, as well as methods of producing and using same, which fully satisfy the objectives and advantages set forth hereinabove. Although the invention has been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed and claimed inventive concept(s).

What is claimed is:

1. A composition comprising an aqueous diagnostic quality control or calibration reagent disposed in a closed system, the composition comprising:
   urea present in a concentration in a range of from about 0.1 mM to about 150 mM;
   at least one buffer; and
   at least one amino acid-containing composition having at least one available primary or secondary amine, the at least one amino acid-containing composition being selected from the group consisting of ornithine and combinations arginine and ornithine, wherein a ratio of urea to the at least one amino acid-containing composition is in a range of from about 0.1:1 to about 100:1, and wherein the pH of the aqueous quality control or calibration reagent varies by +/−1.0 or less of the original pH following storage of the composition, and further wherein formation of ammonia in the aqueous diagnostic quality control or calibration reagent is substantially reduced by at least 20% following storage of the composition when compared to a composition prepared in the absence of the at least one amino acid-containing composition and following storage thereof; and
   wherein the aqueous diagnostic quality control or calibration reagent is for utilization with a diagnostic sensor.

2. The composition of claim 1, wherein a pH variation of +/−1.0 or less of the original pH is observed upon storage under at least one set of storage conditions selected from:
   (a) storage for at least six months at a temperature in a range of from 1° C. to 8° C.;
   (b) storage for at least 6 weeks at a temperature in a range of from 9° C. to 17° C.;
   (c) storage for at least four weeks at a temperature in a range of from 18° C. to 32° C.;
   (d) storage for at least 1 week at a temperature in a range of from 33° C. to 44° C.; and
   (e) storage for at least 24 hours at a temperature in a range of from 45° C. to 50° C.

3. The composition of claim 1, wherein the original pH of the solution is in a range of from about 6 to about 8.

4. The composition of claim 1, wherein a pH variation of +/−0.1 or less of the original pH is observed following storage of the composition.

5. The composition of claim 1, wherein a carbon dioxide concentration of less than 150 mmHg+/−3% is observed following storage of the composition.

6. The composition of claim 1, wherein the concentration of urea in the composition is between about 1.5 mM and about 55 mM.

7. The composition of claim 1, wherein the ratio of urea to the at least one amino acid-containing composition is about 3.57:1.

8. The composition of claim 1, wherein the closed system is a zero head space closed system.

9. The composition of claim 1, wherein the at least one amino acid-containing composition is also the at least one buffer present in the composition.

10. A kit comprising the composition of claim 1.

11. The kit of claim 10, further defined as comprising:
    at least one composition comprising an aqueous diagnostic quality control reagent of claim 1;
    at least one composition comprising an aqueous diagnostic calibration reagent of claim 1; and
    at least one wash solution.

12. A method of stabilizing the pH of an aqueous diagnostic quality control or calibration reagent containing urea and at least one buffer, wherein the original urea concentration of the aqueous diagnostic quality control or calibration reagent is in a range of from about 0.1 mM to about 150 mM, the method comprising the step of:

disposing at least one amino acid-containing composition having at least one available primary or secondary amine, the at least one amino acid-containing composition being selected from the group consisting of ornithine and combinations of arginine and ornithine, into the aqueous diagnostic quality control or calibration reagent such that a ratio of urea to the at least one amino acid-containing composition is in a range of from about 0.1:1 to about 100:1, and whereby the pH of the aqueous quality control or calibration reagent varies by +/−1.0 or less of the original pH following storage of the composition, and further wherein formation of ammonia in the aqueous diagnostic quality control or calibration reagent is substantially reduced by at least 20% following storage of the composition when compared to a composition prepared in the absence of the at least one amino acid-containing composition and following storage thereof; and wherein the aqueous diagnostic quality control or calibration reagent is for utilization with a diagnostic sensor.

13. The method of claim 12, wherein a pH variation of +/−1.0 or less of the original pH is observed upon storage under at least one set of storage conditions selected from:

(a) storage for at least six months at a temperature in a range of from 1° C. to 8° C.;

(b) storage for at least 6 weeks at a temperature in a range of from 9° C. to 17° C.;

(c) storage for at least four weeks at a temperature in a range of from 18° C. to 32° C.;

(d) storage for at least 1 week at a temperature in a range of from 33° C. to 44° C.; and (e) storage for at least 24 hours at a temperature in a range of from 45° C. to 50° C.

14. The method of any of claim 12, wherein a pH variation of +/−0.01 or less of the original pH is observed following storage of the composition.

15. The method of claim 12, wherein the concentration of urea in the composition is between about 1.5 mM and about 55 mM.

16. The method of claim 12, wherein the pKa of at least one amino acid carboxyl group in the at least one amino acid-containing composition is in a range of from about 1.5 to about 2.7.

17. The method of claim 12, wherein the at least one amino acid-containing composition is also the at least one buffer present in the composition.

18. The method of claim 12, wherein the quality control or calibration reagent is utilized with a Blood Urea Nitrogen (BUN) sensor.

* * * * *